(12) United States Patent
Okuda et al.

(10) Patent No.: US 6,997,034 B2
(45) Date of Patent: Feb. 14, 2006

(54) METHOD AND APPARATUS FOR INSPECTING KNOCKING DETECTOR

(75) Inventors: Yoshifumi Okuda, Shiga (JP); Yahiko Iwasaki, Shiga (JP)

(73) Assignee: Daifuku Co., Ltd., Osaka (JP)

( * ) Notice: Subject to any disclaimer, the term of this patent is extended or adjusted under 35 U.S.C. 154(b) by 65 days.

(21) Appl. No.: 10/770,820

(22) Filed: Feb. 3, 2004

(65) Prior Publication Data

US 2004/0154376 A1    Aug. 12, 2004

(30) Foreign Application Priority Data

Feb. 5, 2003 (JP) .............................. 2003-027701

(51) Int. Cl.
*F02P 5/15* (2006.01)
(52) U.S. Cl. ........................ 73/1.82; 73/1.38; 73/35.09
(58) Field of Classification Search ............... 73/35.09, 73/35.11, 1.82, 1.37, 1.38, 117.2, 118.1, 12.01
See application file for complete search history.

(56) References Cited

U.S. PATENT DOCUMENTS 5,421,191 A * 6/1995 Pyko et al. ................. 73/35.09

FOREIGN PATENT DOCUMENTS

JP            05-026778        2/1993

\* cited by examiner

*Primary Examiner*—Robert Raevis
(74) *Attorney, Agent, or Firm*—D. Peter Hochberg; Sean Mellino; Katherine R. Vieyra (57) ABSTRACT

When a knocking detector mounted on a cylinder block of an engine is inspected, the cylinder block is vibrated by a vibrating unit via a housing connected to the cylinder block, and the performance of the knocking detector is judged based on whether or not a peak value of a voltage variation value serving as a detection value of the knocking detector is below a threshold value which has been set based on a peak value of a test voltage variation value serving as a reference value.

13 Claims, 10 Drawing Sheets

METHOD AND APPARATUS FOR INSPECTING KNOCKING DETECTOR

FIELD OF THE INVENTION

The present invention relates to an inspecting method and apparatus for inspecting whether a knocking detector normally operates or not in a tester for an internal combustion engine.

BACKGROUND OF THE INVENTION

A knocking sensor for detecting knocking in an engine is disposed in the cylinder block of an internal combustion engine. An inspection apparatus for inspecting whether such a knocking sensor normally operates or not before an engine is set in a vehicle is conventionally unavailable, though Japanese Patent Laid-Open No. 5-26778 is a conventional document describing an apparatus for detecting abnormality of a knocking sensor.

In conventional engine tests, a continuity test and a diagnosis test for an engine computer are available as a test for a knocking sensor. The continuity test judges whether a sensor is normal by measuring a value of resistance across sensor terminals. The diagnosis test judges whether a sensor is normal by using the output results of failure diagnosis on an engine computer.

However, the continuity test is a one-sided test merely judging whether a value of resistance of a knocking sensor is normal. Thus, an actually measured value may not be properly outputted. Further, in the diagnosis test, a measurement is performed by a knocking sensor in a motoring state in which an engine is ignition operated or a crankshaft and a piston are driven by an external electric motor via an output shaft. An outputted detection vibration value of the knocking sensor may not be constant and is susceptible to disturbance.

According to the conventional document, in the event of an abnormal condition in a knocking sensor when an engine is used, the signal of the knocking sensor is processed, and a standard deviation and an abnormality decision value are compared with each other to decide abnormality of the knocking sensor. When this method is used in a tester for an engine, the decision process becomes extremely complicated.

An object of the present invention is to provide a method and apparatus for inspecting a knocking detector whereby the above-described problem is solved, a constant vibration detection value can be obtained without being affected by disturbance, and whether the knocking detector normally operates is quantitatively decided with ease.

BRIEF SUMMARY OF THE INVENTION

According to one aspect of the invention, when a knocking detector mounted on a cylinder block of an internal combustion engine is inspected, the cylinder block of the internal combustion engine is vibrated in a static state by a vibrator via a transmitting member connected to the cylinder block, and a detection value extracted by the knocking detector is compared with a predetermined reference value to judge the performance of the knocking detector.

According to another aspect of the invention, there are provided with a knocking detector mounted on a cylinder block of an internal combustion engine, a vibrator for vibrating the cylinder block of the internal combustion engine in a static state via a transmitting member connected to the cylinder block, and an inspecting section which compares a detection signal extracted from the knocking detector with a reference value to judge the performance of the knocking detector.

According to the method and apparatus for inspecting the knocking detector, the cylinder block is vibrated by the vibrator via the transmitting member and the detection signal is extracted by the knocking detector in a static state where the internal combustion engine is not ignited or a crankshaft is not rotated. Thus, it is possible to obtain a clear detection signal without being affected by disturbance and to decide more quantitatively and precisely whether the knocking detector normally operates.

According to still another aspect of the invention, the transmitting member is constituted of a housing which covers a driving shaft connected to the output shaft of the cylinder block and makes contact with the cylinder block.

According to the above-described configuration, the cylinder block is indirectly vibrated via the housing making contact with the cylinder block. Thus, even in the case of a different type of an internal combustion engine, the vibrator can be set on a fixed position and can be operated with stability. Further, even when a swinging member such as a harness is suspended from the engine, since a vibration is indirectly created via the housing, it is possible to stably transmit the vibration from the housing to the cylinder block, vibrate the knocking detector under fixed conditions, and conduct an inspection with high precision.

DETAILED DESCRIPTION OF THE PREFERRED EMBODIMENTS

Referring to FIGS. 1 to 10, the following will describe the embodiments of an engine tester comprising an inspection apparatus for a knocking detector.

The engine tester is configured as a motor test bench for testing the performance of an engine serving as an internal combustion engine, for example, before the engine is installed in an automobile and so on. In the motor test bench, the output shaft of the engine is rotationally driven by an electric motor, a crankshaft and a piston are driven without ignition, and the performance of the engine is tested based on the number of revolutions and detected sound.

Figure 4:
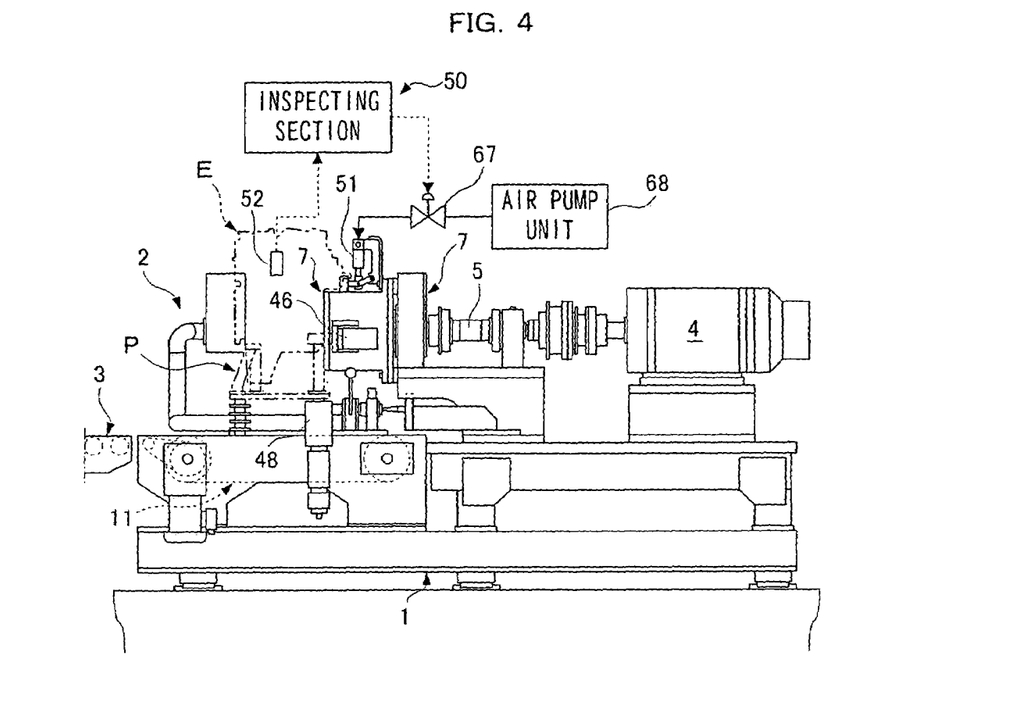
FIG. 4 is a side view showing a motor test bench for a cold test provided with the inspection apparatus.
Figure 5:
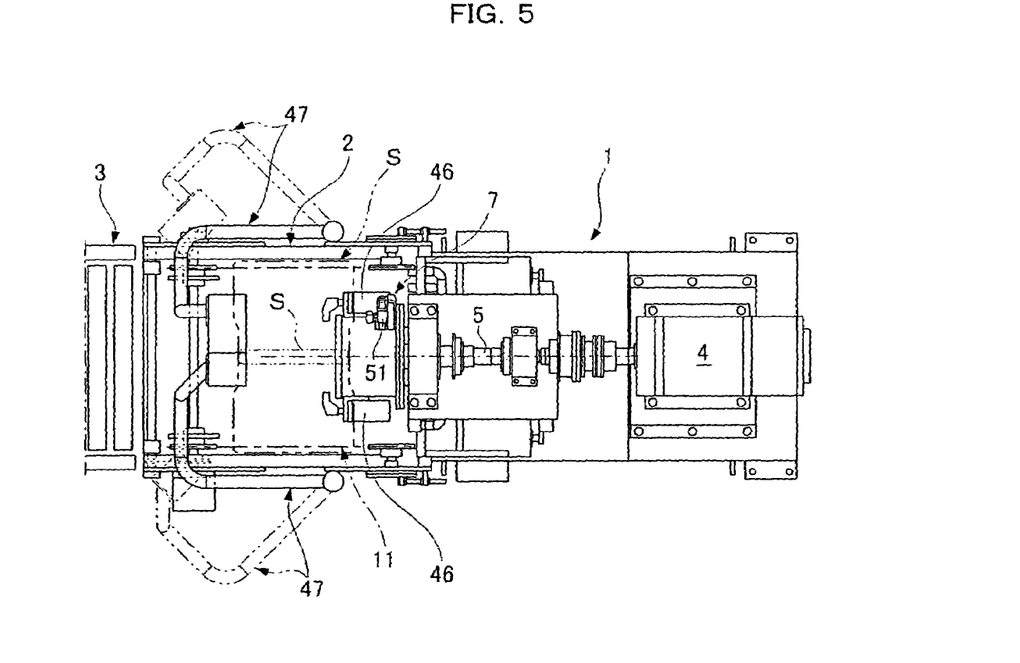
FIG. 5 is a plan view showing the motor test bench.
Figure 6:
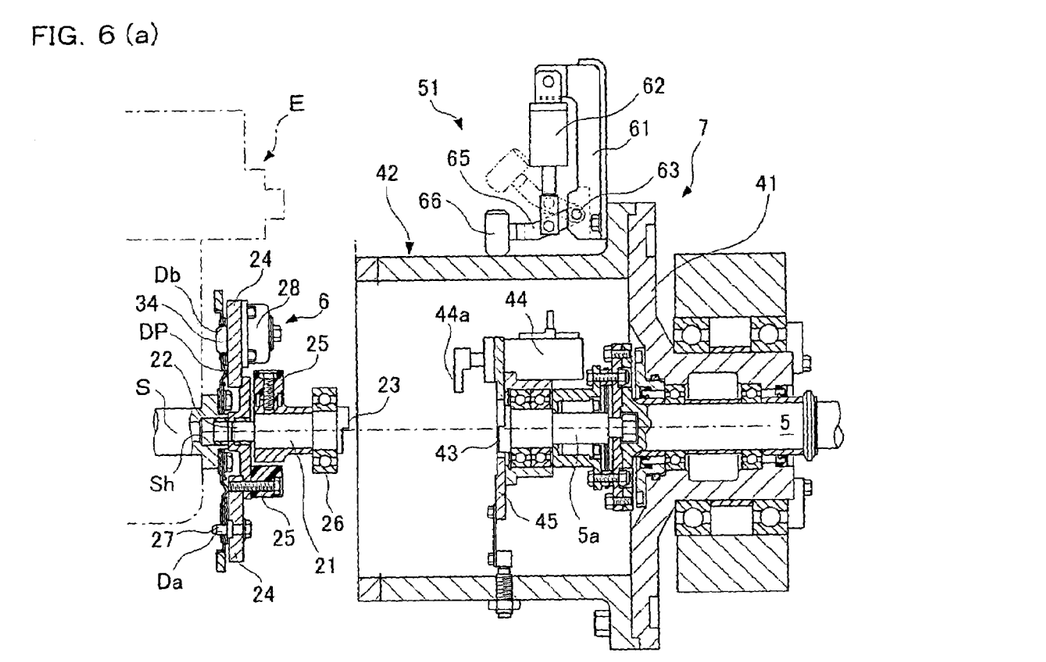
FIG. 6(a) is an exploded sectional side view showing a passive jig and a driving operation part of the motor test bench.
FIG. 6(b) is an assembly sectional side view showing a passive jig and a driving operation part of the motor test bench.

As shown in FIGS. 4 to 6, on a bed 1, the motor test bench comprises engine supporting part 2 where an engine E is disposed with a drive plate for automatic transmission or with a flywheel for manual transmission, an electric motor (rotary driving gear) 4 which rotationally drives a driving shaft 5, and a driving operation part 7 where the driving shaft 5 is connected and fixed to a passive jig 6 mounted on the output shaft S of the engine E. The engine E with a pallet P is carried into the engine supporting part 2 by a conveyor 3.

Figure 9A:
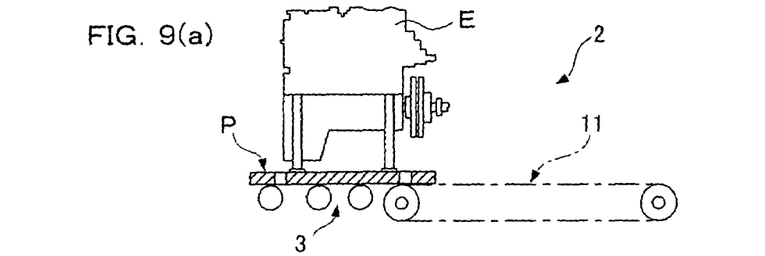
FIGS. 9(a) to 9(d) illustrate the steps of mounting an engine on the motor test bench.
Figure 9B:
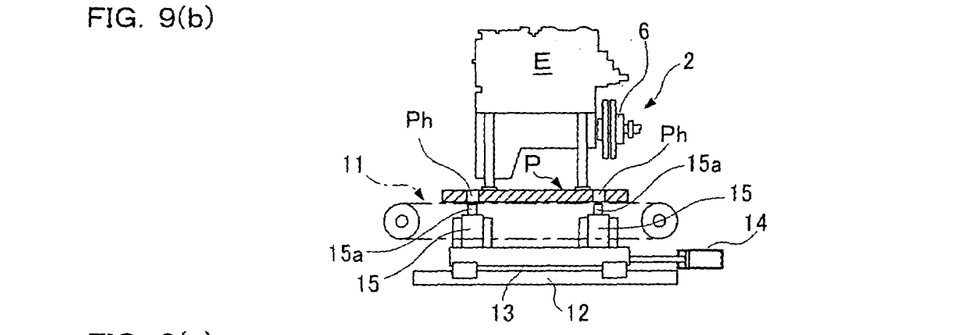

As shown in FIG. 9(b), for example, the engine supporting part 2 comprises a chain-type detachable conveyor 11 that receives the engine E with the pallet P from the conveyor 3 and carries in/out the engine E, a carriage 13 which is movably disposed on a guide rail 12 via a linear bearing in a conveying direction (the axial direction of the driving shaft 5), a drawing cylinder 14 for moving the carriage 13, a plurality of (e.g., four) lift cylinders 15 which are raised on the carriage 13, and positioning pins 15a which are supported by the lift cylinders 15 so as to move vertically and is fit into pin holes Ph on the pallet P.

Figure 9C:
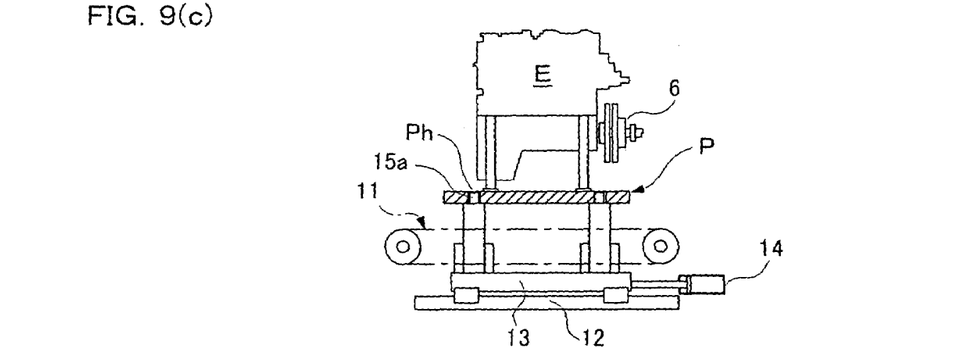
Figure 9D:
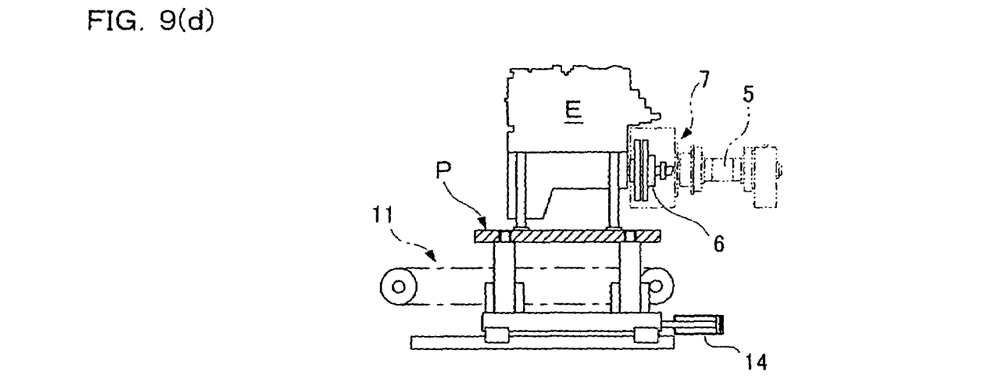

As shown in FIG. 9(a), the pallet P with the engine E is carried into the engine supporting part 2 from the conveyor 3 via the detachable conveyor 11. Then, as shown in FIG. 9(b), a pedestal 16 is lifted by the lift cylinders 15 to fit the positioning pins 15a into the pin holes Ph of the pallet P. Further, as shown in FIG. 9(c), the engine E is lifted by the lift cylinders 15 to a test level where the passive jig 6 coincides with the driving shaft 5. Subsequently as shown in FIG. 9(d), the engine E is moved to the electric motor 4 via the carriage 13 by the drawing cylinder 14 and the back of the engine E and the driving operation part 7 are brought into contact with each other, so that the engine E is loaded in the engine supporting part 2.

As shown in FIG. 6(a), an axial hole Sh is formed on the end of the output shaft S of the engine E and a drive plate DP is attached thereto. On the drive plate DP, a plurality of positioning pin holes Da and retaining holes Db are formed at regular intervals in the circumferential direction.

Figure 7:
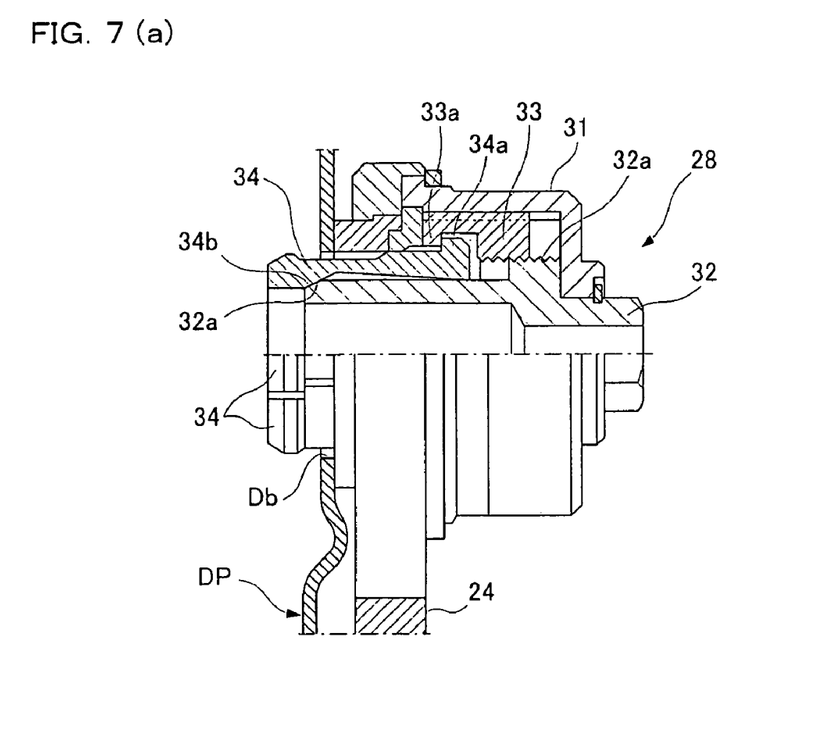
FIG. 7(a) is a half sectional view upon insertion and removal showing a retainer of the driving operation part.
FIG. 7(b) is a half sectional view upon retainment, showing a retainer of the driving operation part.

As shown in FIGS. 6 and 7, the passive jig 6 is mounted beforehand on the end of the output shaft S before a test. A small-diameter portion 22 fit into the center hole of the drive plate DP is formed on one of the ends of a rotating shaft 21, and engaging irregular portion 23 connected to the driving shaft 5 is formed on the other end of the rotating shaft 21. Moreover, the rotating shaft 21 comprises a transmission plate 24 opposed to the drive plate DP, an elastic coupling 25 for connecting the transmission plate 24 and the rotating shaft 21, and an urging bearing 26 which is externally fit and fixed on the engaging irregular portion 23.

On the transmission plate 24, engaging pins 27 fit into the positioning pin holes Da of the drive plate DP are protruded and a retainer 28 fit into the retaining holes Db of the drive plate DP is provided.

As shown in FIG. 7(a), for example, the retainer 28 comprises a rotating operation shaft 32 which is rotationally disposed in a case 31, a moving member 33 which is driven by a screw 32a of the rotating operation shaft 32 so as to protrude/retreat along the axial direction, and split open/close claws 34 which are opened and closed by the movement of the moving member 33 and are retained on the retaining hole Db. Further, since a flange 34a of the open/close claws 34 is engaged to a locking portion 33a of the moving member 33 and the open/close claws 34 are moved according to the movement of the moving member 33, an internal passive portion 34b of the open/close claws 34 is engaged to an open/close tapered portion 32a on the end of the rotating operation shaft 32, so that the open/close claws 34 are opened and closed.

Therefore, the transmission plate 24 opposed to the drive plate DP is brought close to the engine E before the engine E is carried into the engine supporting part 2. Then, the small-diameter portion 22 of the rotating shaft 21 is fit into the center hole of the drive plate DP and the engaging pins 27 are each engaged into the positioning pin holes Da of the drive plate DP. At the same time, the closed open/close claws 34 of the retainer 28 are fit into the engaging holes Db. Then, as shown in FIG. 7(b), the rotating operation shaft 32 is rotated to retreat the moving member 33, so that the open/close claws 34 are opened and are retained on the retaining holes Db and thus the passive jig 6 is mounted and fixed on the output shaft S.

Figure 8A:
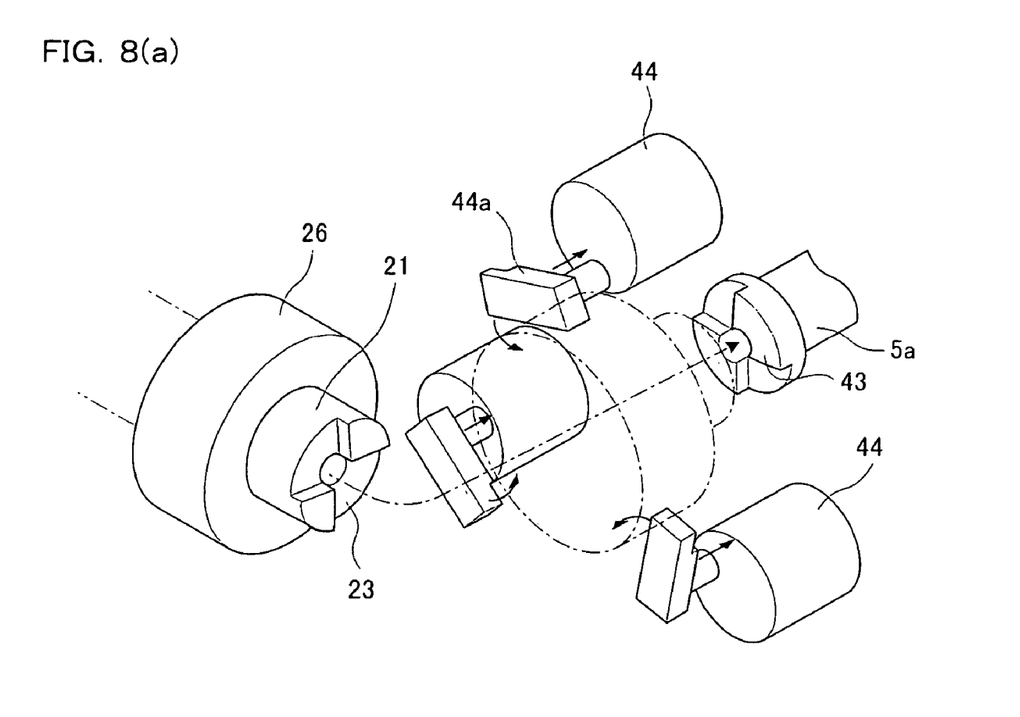
FIG. 8(a) is a perspective view in a separated state showing rotary clamp cylinders of the driving operation part.

The elastic coupling 25 is configured so that a displacement between the transmission plate 24 and the rotating shaft 21 in the diameter direction and a change in torque in the rotating direction are absorbed by an elastic member such as a synthetic rubber. Further, as shown in FIG. 8(a), for example, the engaging irregular portion 23 has adjacent concave portions and convex portions that are shaped like sectors having end faces split at 90°.

Figure 8B:
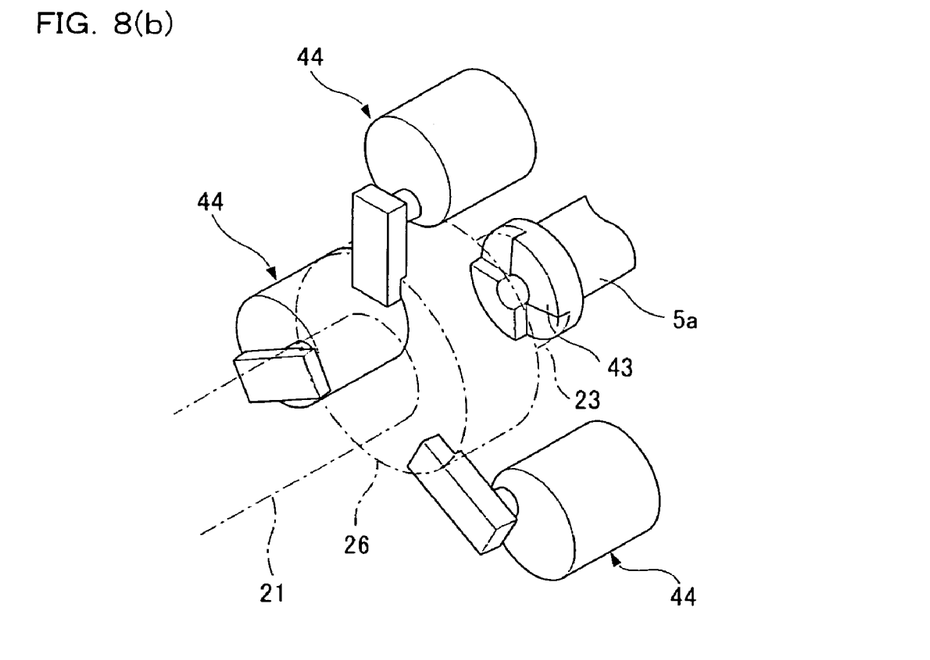
FIG. 8(b) is a perspective view in a connected state showing rotary clamp cylinders of the driving operation part.

As shown in FIG. 6(a), for example, the driving operation part 7 has a flange plate 41 which is provided on the end of the driving shaft 5 via a bearing and a housing 42 which is attached to the flange plate 41 so as to cover the driving shaft 5. Further, an engaged irregular portion 43 to be fit into the engaging irregular portion 23 of the rotating shaft 21 is formed on the connecting shaft (driving shaft) 5a which is connected and fixed to the end of the driving shaft 5. Moreover, a fixing member 45 is attached to the connecting shaft 5a via the bearing and a plurality of rotary clamp cylinders (three in FIG. 6) 44 are provided on the fixing member 45. The rotary clamp cylinders 44 are provided to connect and fix the rotating shaft 21 and the connecting shaft 5a, and dampers 44a are attached to the output ends of the rotary clamp cylinders 44. The output ends can freely protrude/retreat and rotate. As shown in FIGS. 8(a) and 8(b), the dampers 44a are engaged to the urging bearing 26, which is provided on the rotating shaft 21, to draw the passive jig 6, so that the engaging irregular portion 23 of the rotating shaft 21 can be connected and fixed to the engaged irregular portion 43 of the connecting shaft 5.

As shown in FIGS. 4 and 5, the housing 42 comprises a vibrating unit (vibrator) 51 of the inspection apparatus for the knocking detector of the present invention on the outer circumference, and a plurality of lock cylinders 46 which draw the engine E and the pallet P by using locking arms 46a and bring the housing 42 into contact with the engine E. Any swinging member is not suspended from the housing 42. Reference numeral 47 denotes an arm type safety cover which covers a pulley and so forth at the front of the engine E, and reference numeral 48 denotes a junction device for transmitting and receiving an electric signal and a power supply to and from the engine E.

Therefore, when the engine E is positioned on a predetermined position of the engine supporting part 2, the engaging irregular portion 23 of the rotating shaft 21 and the engaged irregular portion 43 of the connecting shaft 5 that have been opposed to each other are positioned, the engaging irregular portion 23 and the engaged irregular portion 43 are brought closer to each other by the drawing cylinder 14, and the locking arms 46a are rotated by the rotary clamp cylinders 44 and are engaged and drawn to the locking bearing 26, so that the engaging irregular portion 23 and the engaged irregular portion 43 are fit into each other to connect the rotating shaft 21 and the connecting shaft 5a. Further, the housing 42 of the driving operation part 7 and the engine E are fixed to each other in an intimate contact by the lock cylinders 46. Moreover, the pulley and so forth at the front of the engine E is covered with the safety cover 47 and the junction device 48 is connected.

To the engine E having a ring gear on the output shaft S, the output shaft S and the driving shaft 5 may be connected by, instead of the drive plate DP, a rotating shaft engaged to the shaft hole of the output shaft and a chuck having a plurality of engaging member engaged to the teeth of the ring gear.

Figure 1:
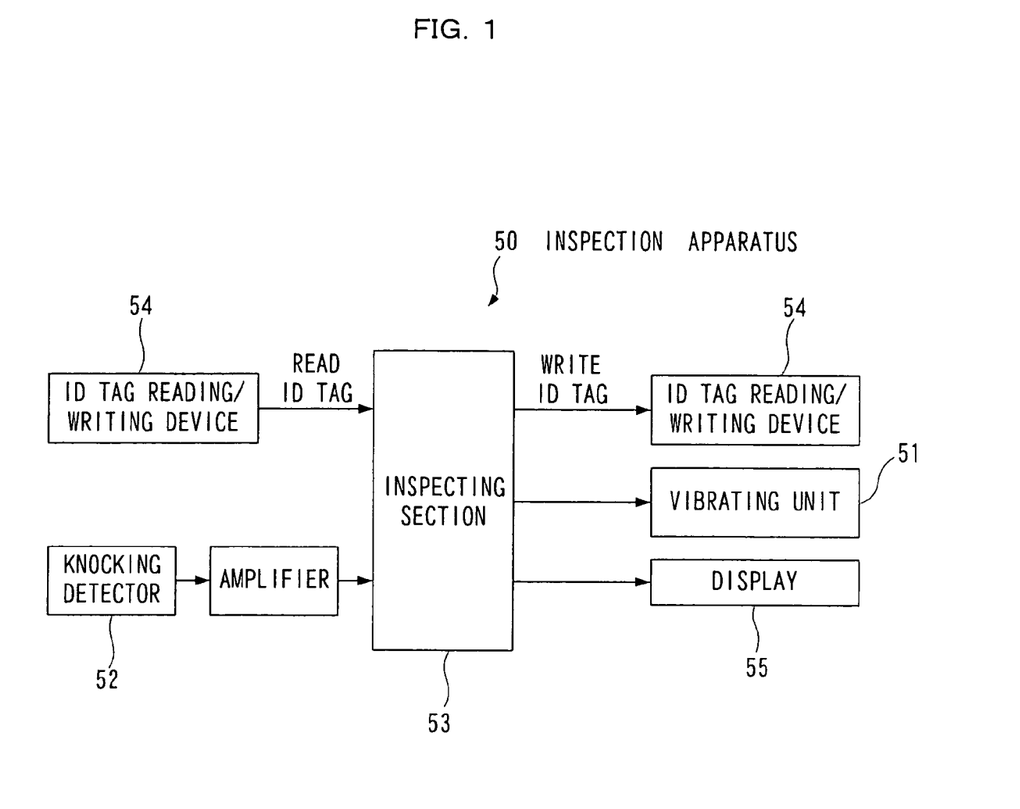
FIG. 1 is a structural diagram showing one embodiment of an inspection apparatus for a knocking detector according to the present invention.

An inspection apparatus 50 for the knocking detector quantitatively inspects whether a knocking detector 52 normally operates at the center of a cylinder block of the engine E, before the output shaft of the engine is rotationally driven by the electric motor 4, the crankshaft and the piston are driven without ignition, and the performance of the engine is tested based on the number of revolutions and detected sound. As shown in FIG. 1, the inspection apparatus 50 comprises the knocking detector 52, the vibrating unit 51, and an inspecting section 53. The knocking detector 52 detects a vibration of the cylinder block when hammering is performed by the vibrating unit 51. Then, the inspecting section 53 judges whether the knocking detector 52 is normal based on a detection value. The inspection apparatus 50 further comprises an ID tag reading/writing device 54 which reads the ID tag of the engine E and writes an inspection result, a display 55 for displaying the result of the inspecting section 53, and an output device such as a printer.

Figure 10A:
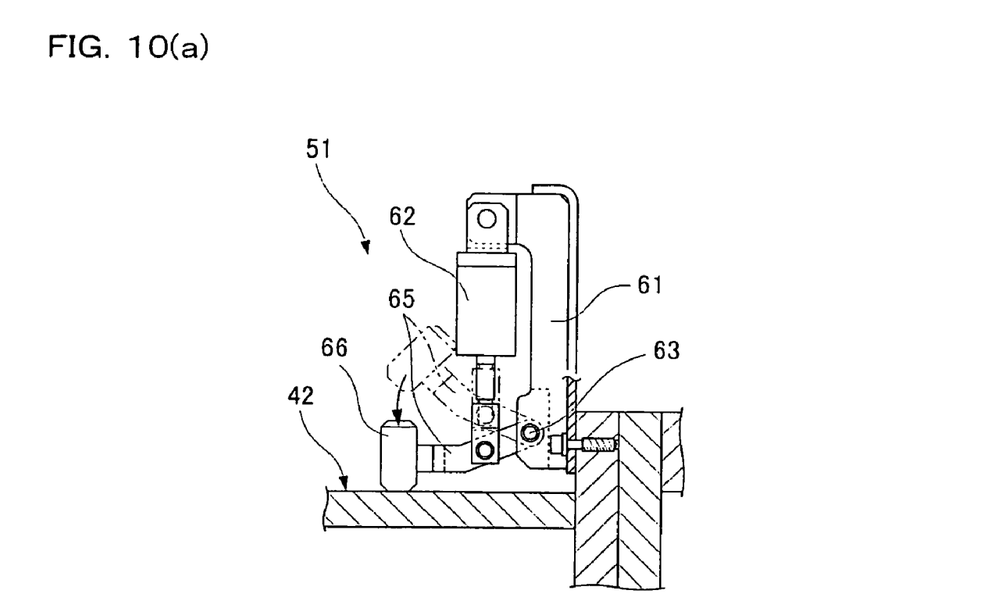
FIG. 10(a) is a side view of the present invention showing a vibrating unit of the driving operation part.
Figure 10B:
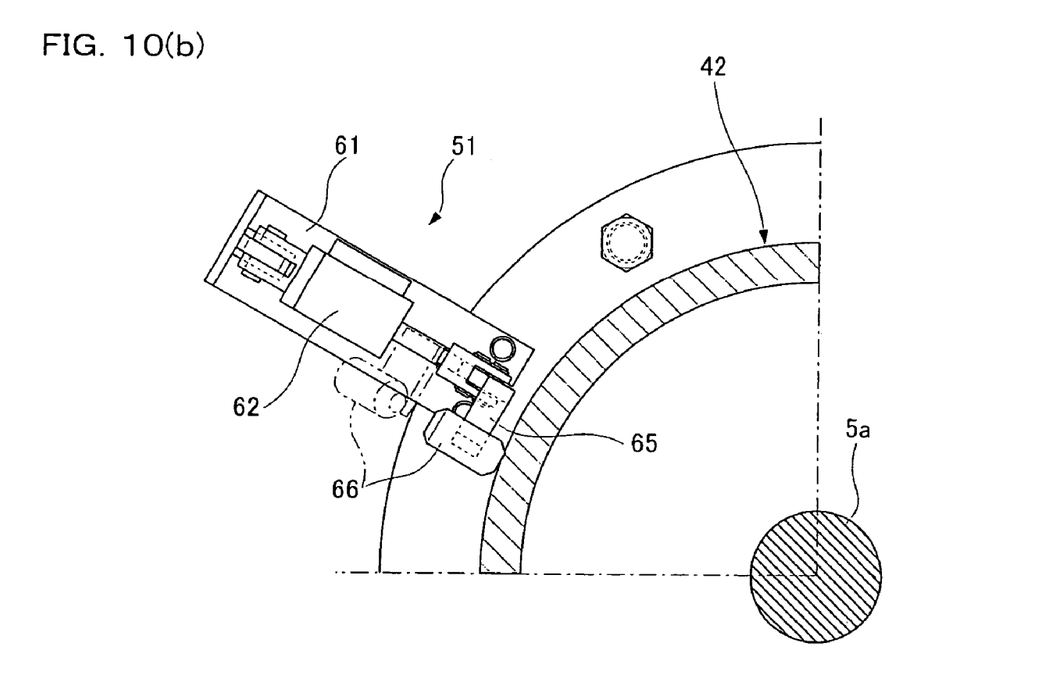
FIG. 10(b) is a front view of the present invention showing a vibrating unit of the driving operation part.

As shown in FIGS. 4 and 10, the vibrating unit 51 comprises an air driven knocker cylinder 62 attached to the housing 42 via an attaching member 61, a knocker arm 65 rotationally supported on the bracket of the attaching member 61 via a pin 63 provided in the tangential direction of the housing 42 (or rotating shaft 21), and a knocker weight 66 attached to the free end of the knocker arm 65. The piston rod of the knocker cylinder 62 is pin-connected at the midpoint of the knocker arm 65.

Thus, an air supply valve 67 is operated and vibrating air is supplied from an air pump unit 68 to the knocker cylinder 62, so that the piston rod is moved. Hence, the knocker arm 65 is rotated, the knocker weight 66 hits the housing 42 and creates a vibration, and the vibration is transmitted from the housing 42 to the cylinder block of the engine E and is detected by the knocking detector 52.

Figure 2:
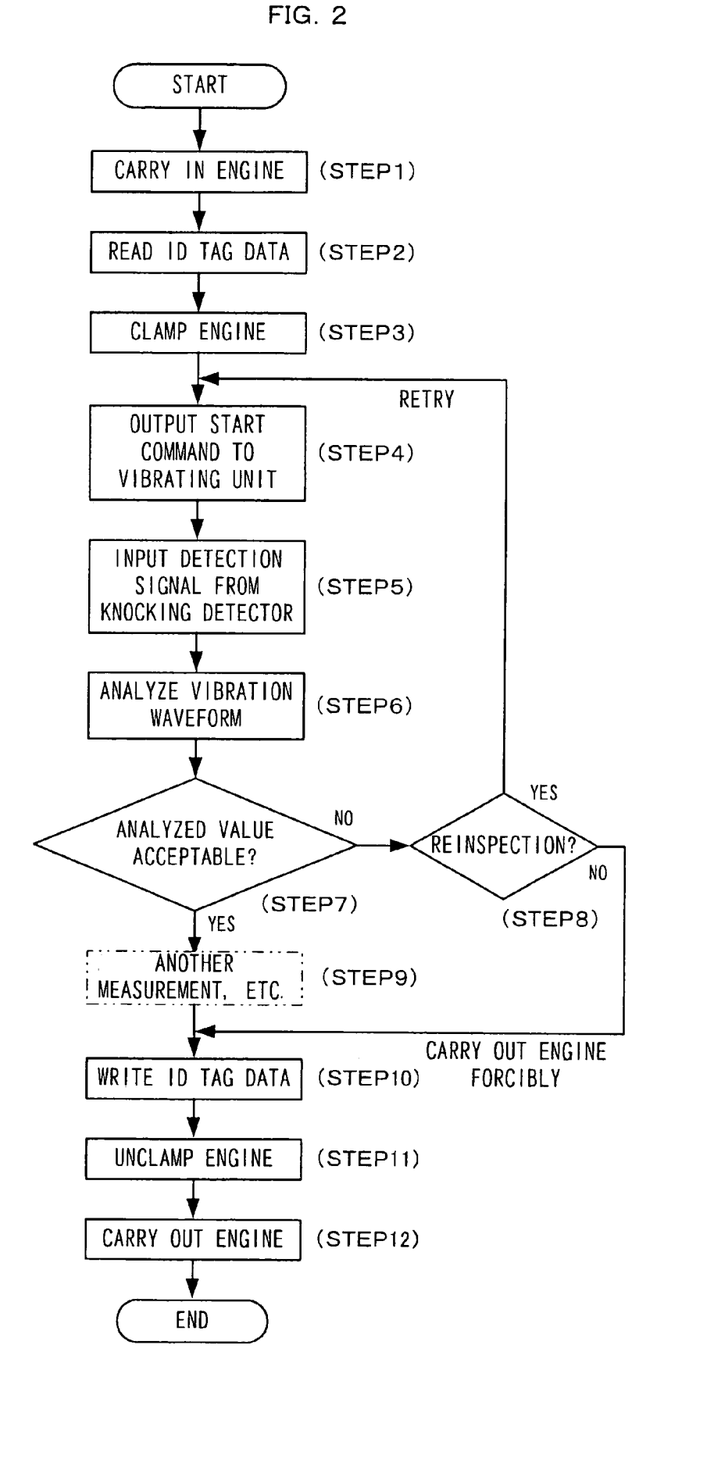
FIG. 2 is a flowchart showing the operations of an inspecting section.
Figure 3:
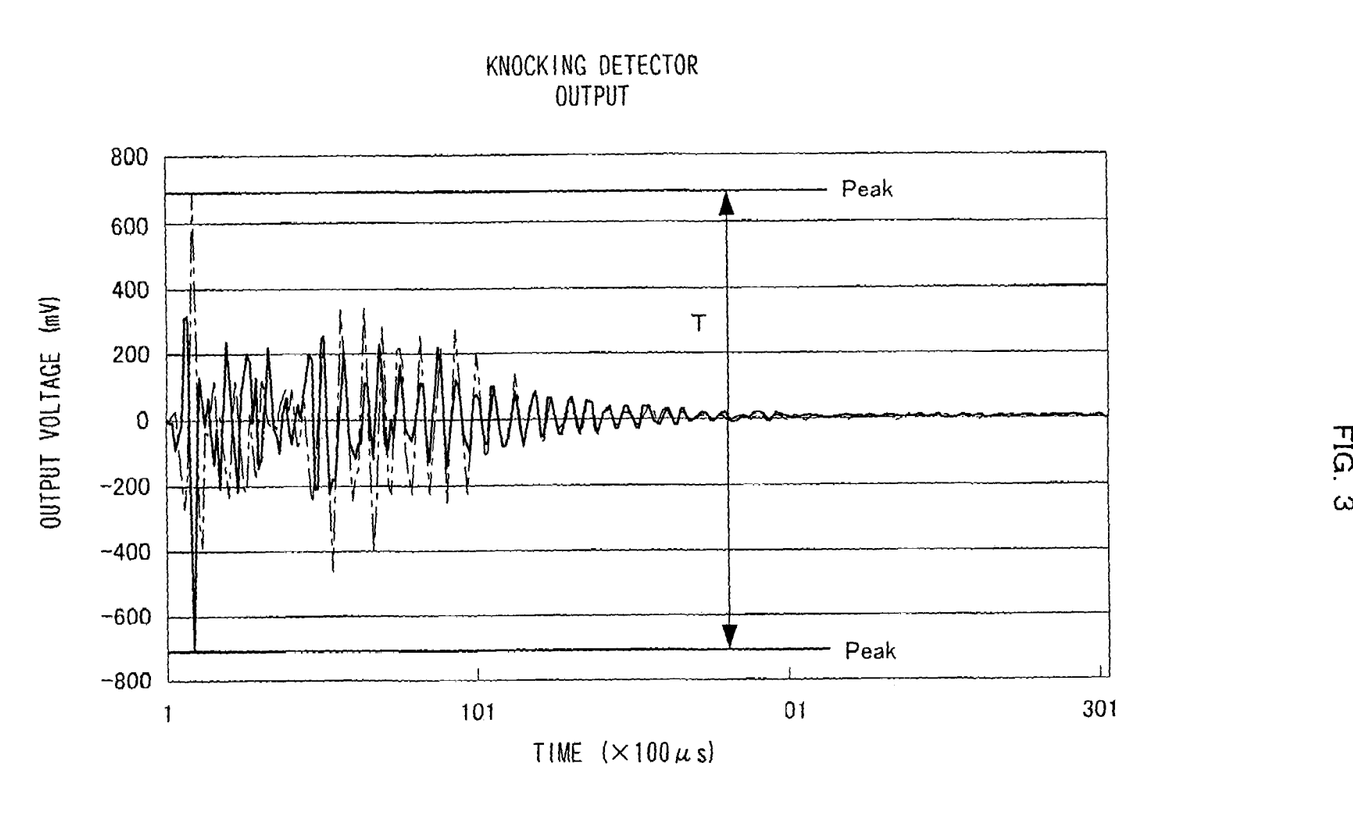
FIG. 3 is a graph showing a specific example of a vibration waveform in the inspecting section.

Referring to FIGS. 2 and 3, the following will describe a method of inspecting the knocking detector.

(STEP 1) The engine E is carried into the engine supporting part 2 by the conveyor 3.

(STEP 2) The ID tag of the carried engine E is read by the ID tag reading/writing device 54 and the data is inputted to the inspecting section 53.

(STEP 3) The engine E is positioned and fixed, and the rotating shaft 21 of the passive jig 6 having been attached to the engine E is connected to the connecting shaft 5 of the driving operation part 7.

(STEP 4) A start command is outputted from the inspecting section 53 to the vibrating unit 51, the knocker cylinder 62 is driven, and the housing 42 is subjected to hammering (vibration) by the knocker weight 66.

(STEP 5) A detection signal (detection value) is inputted from the knocking detector 52 to the inspecting section 53.

(STEP 6) A vibration waveform detected by the inspecting section 53 is subjected to waveform analysis.

(STEP 7) In the inspecting section 53, a test vibration waveform (reference value) having been obtained from a normal knocking detector 52 of a similar engine E is compared with the detected vibration waveform (detection value), and it is quantitatively judged whether the detected vibration waveform indicates acceptable performance of a proper operation or rejected performance.

That is, for example as shown in FIG. 3, a first method of deciding acceptable performance is a peak-to-peak method in the inspecting section 53. In this method, a threshold value T is determined from an actual test vibration waveform (reference value), that is the peak value of a test voltage variation value. In the case of the peak value of a detected vibration waveform>the threshold value T, acceptance is decided. In the case of the peak value of a detected vibration waveform<the threshold value T, rejection is decided.

Further, a second method of deciding an acceptable performance is an envelope determination method (pattern matching) in the inspecting section 53. In this method, for example, a variation pattern having a varied peak value is formed from an output voltage variation by using an envelope tool, the variation pattern of a test vibration waveform (reference value) and the variation pattern of a detected vibration waveform are overlapped, and acceptance or rejection is decided based on whether an overlapping area is larger than a set matching amount (threshold value).

(STEP 8) When rejection is decided in an inspection of the knocking detector 52, the inspection of the knocking detector 52 is repeated only a predetermined number of times. When rejection is decided again after the predetermined number of inspections, the engine E is forcibly carried.

(STEP 9) When acceptance is decided in an inspection of the knocking detector 52, another measuring test is conducted. This test is not conducted when the engine E is forcibly carried.

(STEP 10) The inspection data of the knocking detector 52 and the inspection data of another test are written in an ID tag via the ID tag reading/writing device 54. The written data is outputted to the display 55 and is displayed thereon if necessary.

(STEP 11) The rotating shaft 21 and the driving shaft 5 are separated from each other and the engine E is unlocked.

(STEP 12) The engine E is carried out from the engine supporting part 2 by the conveyor 3.

According to the above-described embodiment, in a state in which the engine E is not ignited, the cylinder block is indirectly vibrated by the vibrating unit 51 and a detection signal is extracted by the knocking detector 52. Thus, it is possible to extract a clear detection signal without being affected by disturbance and to quantitatively and precisely decide whether the knocking detector 52 is normal.

Further, since the cylinder block is vibrated by the vibrating unit 51 via the housing 42, the vibrating unit 51 is stably set on a fixed position and the cylinder block is stably vibrated via the housing 42. Moreover, even in the event of a swinging member (harness, etc.) which suspends from the engine E and interferes with vibration, a vibration is created via the housing 42 and thus a test vibration can be stably transmitted from the housing 42 to the cylinder block, so that the knocking detector 52 is operated under fixed conditions and an inspection is performed with high precision.

In the above-described embodiment, an inspection is conducted before another test. An inspection may be performed after another test.

In the above-described embodiment, installation is performed on the motor test bench for a cold test but installation can be performed on the running bench for testing when the engine is ignited. Also in this case, the test of the knocking detector is conducted while the engine is not ignited before or after the test.

Figure 11:
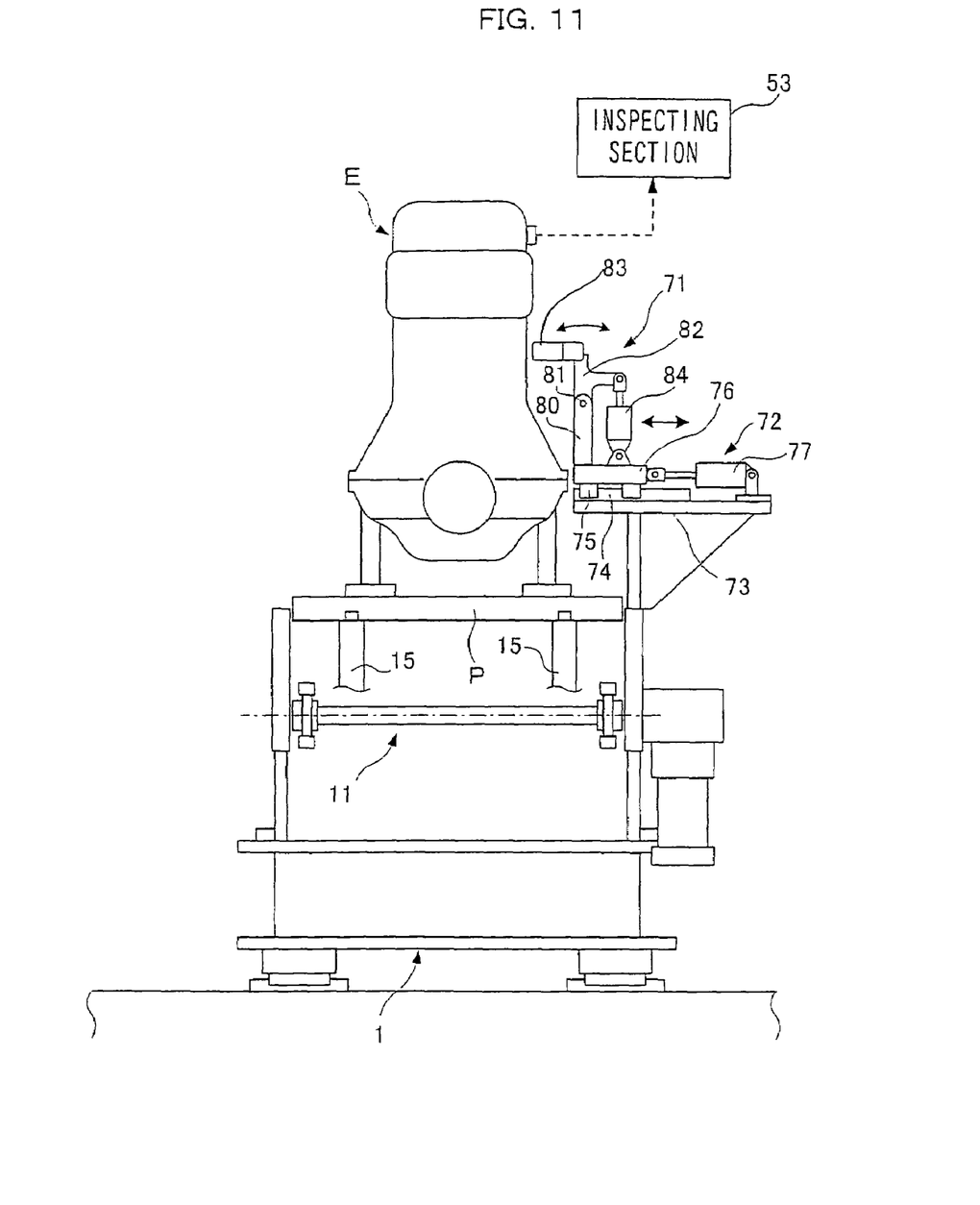
FIG. 11 is a rear view of a motor test bench, showing a second embodiment of an inspection apparatus for a knocking detector according to the present invention.

In the first embodiment, hammering is performed on the housing 42 by the vibrating unit 51 to indirectly vibrate the knocking detector 52 of the cylinder block. In the second embodiment, hammering is directly performed on a cylinder block of an engine E by a vibrating unit 71 and creates a vibration. The same members as Embodiment 1 are indicated by the same reference numerals and the explanation thereof is omitted.

The vibrating unit 71 is provided on a frame on one side of a detachable conveyor 11, which is mounted on a bed 1, via a vibrating position adjusting device 72. That is, based on the data of an ID tag of the engine E that is inputted to an inspecting section 53, the vibrating position adjusting device 72 adjusts the knocking position of a cylinder block according to an engine type. A guide rail 74 is provided on an installation stand 73 orthogonally to the conveying direction of the detachable conveyor 11, and a support 76 is disposed on the guide rail 74 via a linear bearing 75 so that the position of the support 76 is freely adjusted. A position adjusting cylinder 77 operated in response to an operation signal from the inspecting section 53 is disposed on the installation stand 73, and the piston rod of the position adjusting cylinder 77 is connected to the support 76.

On the support 76, a knocker arm 82 is rotationally supported on a bracket 80 via a horizontal shaft 81, and a knocker weight 83 is attached to the end of the knocker arm 82. Further, the piston rod of the knocker cylinder 84, which is swingably supported on the support 76, is pin-connected to the protrusion of the knocker arm 82.

Therefore, when the engine E is carried from a conveyor 3 via a detachable conveyor, the position adjusting cylinder 77 is operated in response to a command from the inspecting section 53 according to the type of the engine E, and the support 76 is moved to adjust the knocking position of the cylinder block. When the engine E is fixed in an engine supporting part 2 by lift cylinders 15, a start command is outputted from the inspecting section 53 to the vibrating unit 71, the knocker cylinder 84 is driven, and the cylinder block is hit by a knocker weight 83, so that hammering (vibration) is performed.

The subsequent process is performed according to the first embodiment.

According to the above-described embodiment, the cylinder block is directly vibrated by the vibrating unit 71 and a detection signal is extracted by the knocking detector 52 in a state in which the engine E is not ignited. Thus, it is possible to extract a clear detection signal without being affected by disturbance and to quantitatively and precisely decide whether the knocking detector 52 is normal.

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

We claim:

1. A method for inspecting a knocking detector, comprising the steps of:
   when the knocking detector mounted on a cylinder block of an internal combustion engine is inspected,
   vibrating the cylinder block of the internal combustion engine in a static state by a vibrator via a transmitting member connected to the cylinder block; and
   comparing a detection value extracted by the knocking detector with a pre-determined reference value to judge performance of the knocking detector.

2. The method for inspecting the knocking detector according to claim 1, wherein the performance of the knocking detector is judged based on whether or not a peak value of a voltage variation value serving as a detection value of the knocking detector is below a threshold value, which is set based on a peak value of a test voltage variation value serving as a reference value.

3. The method for inspecting the knocking detector according to claim 1, wherein the performance of the knocking detector is judged based on whether or not a waveform pattern of a voltage variation value serving as a detection value of the knocking detector matches a waveform pattern of a test voltage variation value serving as a reference value.

4. A method for inspecting a knocking detector, comprising the steps of:
   when the knocking detector mounted on a cylinder block of an internal combustion engine is inspected;
   directly vibrating the cylinder block of the internal combustion engine in a static state by a vibrator; and
   comparing a detection value extracted by the knocking detector with a pre-determined reference value to judge performance of the knocking detector.

5. The method for inspecting the knocking detector according to claim 4, wherein the performance of the knocking detector is judged based on whether or not a peak value of a voltage variation value serving as a detection value of the knocking detector is below a threshold value, which is set based on a peak value of a test voltage variation value serving as a reference value.

6. The method for inspecting the knocking detector according to claim 4, wherein the performance of the knocking detector is judged based on whether or not a waveform pattern of a voltage variation value serving as a detection value of the knocking detector matches a waveform pattern of a test voltage variation value serving as a reference value.

7. An inspection apparatus for a knocking detector, comprising:
   a knocking detector mounted on a cylinder block of an internal combustion engine;
   a vibrator for vibrating the cylinder block of the internal combustion engine in a static state via a transmitting member connected to the cylinder block; and
   an inspecting section for comparing a detection signal extracted from the knocking detector with a reference value to judge performance of the knocking detector.

8. The inspection apparatus for the knocking detector according to claim 7, wherein the transmitting member comprises a housing covering a driving shaft connected to an output shaft of the cylinder block and making contact with the cylinder block.

9. The inspection apparatus for the knocking detector according to claim 7, wherein the inspecting section judges the performance of the knocking detector based on whether or not a peak value of a voltage variation value serving as a detection value of the knocking detector is below a threshold value, which is set based on a peak value of a test voltage variation value serving as a reference value.

10. The inspection apparatus for the knocking detector according to claim 7, wherein the inspecting section judges the performance of the knocking detector based on whether or not a waveform pattern of a voltage variation value serving as a detection value of the knocking detector matches a waveform pattern of a test voltage variation value serving as a reference value.

11. An inspection apparatus for a knocking detector, comprising:

a knocking detector mounted on a cylinder block of an internal combustion engine;

a vibrator for directly vibrating the cylinder block of the internal combustion engine in a static state; and an inspecting section for comparing a detection signal extracted from the knocking detector with a reference value to judge performance of the knocking detector.

12. The inspection apparatus for the knocking detector according to claim 11, wherein the inspecting section judges the performance of the knocking detector based on whether or not a peak value of a voltage variation value serving as a detection value of the knocking detector is below a threshold value, which is set based on a peak value of a test voltage variation value serving as a reference value.

13. The inspection apparatus for the knocking detector according to claim 11, wherein the inspecting section judges the performance of the knocking detector based on whether or not a waveform pattern of a voltage variation value serving as a detection value of the knocking detector matches a waveform pattern of a test voltage variation value serving as a reference value.

* * * * *